US012806006B2

(12) United States Patent
Wen et al.

(10) Patent No.: US 12,806,006 B2
(45) Date of Patent: Nov. 24, 2026

(54) SINUS AND NASAL STENT

(71) Applicant: Medtronic Xomed, Inc., Jacksonville, FL (US)

(72) Inventors: Jie Wen, Santa Rosa, CA (US); Dana A. Oliver, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 573 days.

(21) Appl. No.: 18/369,604

(22) Filed: Sep. 18, 2023

(65) Prior Publication Data

US 2024/0000562 A1 Jan. 4, 2024

Related U.S. Application Data

(63) Continuation of application No. 15/750,688, filed as application No. PCT/US2016/049042 on Aug. 26, 2016, now Pat. No. 11,759,314.

(60) Provisional application No. 62/210,267, filed on Aug. 26, 2015.

(51) Int. Cl.

| | |
|---|---|
| ***A61F 2/90*** | (2013.01) |
| ***A61F 2/07*** | (2013.01) |
| ***A61F 2/18*** | (2006.01) |
| ***A61F 2/966*** | (2013.01) |
| *A61B 17/24* | (2006.01) |

(52) U.S. Cl.

CPC ................ *A61F 2/186* (2013.01); *A61F 2/07* (2013.01); *A61F 2/90* (2013.01); *A61F 2/966* (2013.01); *A61B 17/24* (2013.01); *A61F 2002/075* (2013.01); *A61F 2250/0039* (2013.01)

(58) Field of Classification Search

CPC ........ A61F 2/18; A61F 2/90; A61F 2002/183; A61B 17/24

See application file for complete search history.

(56) References Cited

U.S. PATENT DOCUMENTS

| | | | | |
|---|---|---|---|---|
| 5,843,158 | A | 12/1998 | Lenker et al. | |
| 8,585,731 | B2 | 11/2013 | Abbate et al. | |
| 10,357,640 | B2 * | 7/2019 | Abbate .................... | A61F 5/08 |

(Continued)

FOREIGN PATENT DOCUMENTS

| | | | |
|---|---|---|---|
| CN | 2526020 | Y | 12/2002 |
| CN | 102512272 | A | 6/2012 |

(Continued)

OTHER PUBLICATIONS

Canadian Office Action issued in corresponding Canadian Application No. 2,996,539 dated Sep. 2, 2022, 3 pages.

(Continued)

*Primary Examiner* — Brian A Dukert

(74) *Attorney, Agent, or Firm* — Carter, DeLuca & Farrell, LLP

(57) ABSTRACT

A stent that is sleeved and radially expandable, and which in an expanded state provides a breathable, generally tubular structure sized and shaped for residence in a sinus or nasal cavity or passage, and in an unexpanded state has a cross-sectional diameter suitable for insertion into such cavity or passage. The sleeve limits expansion and outward pressure exerted by the stent and thereby can prevent or reduce the incidence of headache in patients, and can provide increased surface area for improved elution of chugs to nearby mucosal tissue.

20 Claims, 11 Drawing Sheets

(56) References Cited

U.S. PATENT DOCUMENTS

| | | | |
|---|---|---|---|
| 10,912,663 | B2 | 2/2021 | Yaniv et al. |
| 11,759,314 | B2 | 9/2023 | Wen et al. |
| 2004/0116958 | A1 | 6/2004 | Gopferich et al. |
| 2007/0014830 | A1 | 1/2007 | Tijsma et al. |
| 2007/0110788 | A1 | 5/2007 | Hissong et al. |
| 2007/0264310 | A1 | 11/2007 | Hissong et al. |
| 2009/0204196 | A1 | 8/2009 | Weber |
| 2011/0125091 | A1 | 5/2011 | Abbate |
| 2014/0079755 | A1 | 3/2014 | Eaton et al. |
| 2014/0283349 | A1 | 9/2014 | Abbate et al. |
| 2015/0100133 | A1 | 4/2015 | Xie et al. |

FOREIGN PATENT DOCUMENTS

| | | | |
|---|---|---|---|
| CN | 102573981 | A | 7/2012 |
| CN | 102988122 | B | 11/2013 |
| JP | H08280722 | A | 10/1996 |
| JP | 3597908 | B2 | 12/2004 |
| WO | 2013097261 | A1 | 7/2013 |

OTHER PUBLICATIONS

International Search Report and Written Opinion for PCT/US2016/049042 dated Jan. 11, 2017.
First Office Action for counterpart Chinese Application No. 201680049217.9, dated Jun. 21, 2019.

* cited by examiner

SINUS AND NASAL STENT

CROSS-REFERENCE TO RELATED APPLICATION

This application is a continuation of U.S. patent application Ser. No. 15/750,688, filed on Feb. 6, 2019, which is a National Stage Entry of PCT Application No. PCT/US2016/049042, filed Aug. 26, 2016, which claims the benefit of U.S. Provisional Application Ser. No. 62/210,267 filed Aug. 26, 2015 and entitled "SINUS AND NASAL STENT", the entire disclosure of each of which is incorporated herein by reference.

TECHNICAL FIELD

This invention relates to the treatment of sinus and nasal conditions using implantable stents.

BACKGROUND

Sinusitis is a condition characterized by inflammation of the mucosal lining of the sinuses. Current therapies include corticosteroid treatment to reduce inflammation, and surgical treatment to remove inflamed tissue. After surgery, steroid treatment may be needed to reduce post-surgical inflammation. Traditional oral administration of steroids typically is not effective. Penetration of these systemically delivered agents into the sinus mucosa can be limited due to poor blood flow to the sinuses. Topical applications such as sprays, creams or gels may also be ineffective due to factors such as failure of the steroid to travel far enough to reach the affected sinus due to obstructed ostia, or short contact with the sinus mucosa and consequent low absorption of the steroid. A currently preferred device for local delivery of steroids in the sinuses is a biodegradable drug-eluting stent. However, when such stents degrade, they can break into small pieces and generate acidic degradation byproducts, causing irritation to the sinus tissues. If removal of the stent is needed due to complications such as late stage inflammation or headache, the degradation may make it difficult to cleanly remove the stent. Removal may also require that the patient undergo the inconvenience and expense of a return visit to the surgeon.

For some sinus and nasal stent designs, it can also be difficult to provide a proper balance of compressed size, expanded size, and expansion force, especially if the stent must also provide drug-eluting or biodegradable features.

SUMMARY OF THE INVENTION

The invention provides in one aspect a stent that is sleeved and radially expandable, and which in an expanded state provides a breathable, generally tubular structure sized and shaped for residence in a sinus or nasal cavity or passage, and in an unexpanded state has a cross-sectional diameter suitable for insertion into such cavity or passage. The stent typically will include two elements, namely a radially expandable inner element which may be referred to as the "base stent", and an outer element surrounding and constraining at least a portion of the base stent and which may be referred to as the "sleeve". When assembled together, these two elements may be referred to as the "stent". The base stent and sleeve desirably have a reduced tendency to cause headaches in patients compared to an otherwise similar base stent that does not include such a sleeve.

The invention provides in another aspect a stent for use in the treatment of sinusitis, the stent being sleeved and radially expandable, and in an expanded state providing a breathable, generally tubular structure sized and shaped for residence in a sinus or nasal cavity or passage, and in an unexpanded state having a cross-sectional diameter suitable for insertion into such cavity or passage.

The invention provides in yet another aspect a sinus or nasal stent insertion device or inserter comprising:

a) a proximal grip portion configured to be grasped outside a patient;
b) a distal hollow tubular portion configured to be manipulated using the grip portion and sized for insertion of a stent disposed within the hollow tubular portion into a sinus or nasal cavity or passage in a patient;
c) one or more sleeved, radially expandable stents disposed in an unexpanded state within the hollow tubular portion, having a cross-sectional diameter suitable for insertion into such sinus or nasal cavity or passage, and in an expanded state providing a breathable, generally tubular structure sized and shaped for residence in such cavity or passage; and
d) an actuator disposed within the inserter and configured to deliver one or more of the stents from the hollow tubular portion into such cavity or passage.

The invention provides in yet another aspect a method for sinus or nasal treatment, the method comprising:

a) providing a sinus or nasal stent inserter comprising:
   i) a proximal grip portion configured to be grasped outside a patient;
   ii) a distal hollow tubular portion configured to be manipulated using the grip portion and sized for insertion of a stent disposed within the hollow tubular portion into a sinus or nasal cavity or passage in a patient;
   iii) one or more sleeved, radially expandable stents disposed in an unexpanded state within the hollow tubular portion, having a cross-sectional diameter suitable for insertion into such sinus or nasal cavity or passage, and in an expanded state providing a breathable, generally tubular structure sized and shaped for residence in such cavity or passage; and
   iv) an actuator disposed within the inserter and configured to deliver one or more of the stents from the hollow tubular portion into such cavity or passage;
b) manipulating the grip portion to advance the distal portion into a stentable sinus or nasal cavity or passage; and
c) activating the actuator to deliver one or more of the stents from the hollow tubular portion into such stentable sinus or nasal cavity or passage.

BRIEF DESCRIPTION OF THE DRAWING

Like reference symbols in the various figures of the drawing indicate like elements. The elements in the drawing are not to scale.

DETAILED DESCRIPTION

The following detailed description discusses certain embodiments and is not to be taken in a limiting sense. All weights, amounts and ratios herein are by weight, unless otherwise specifically noted.

Figure 1:
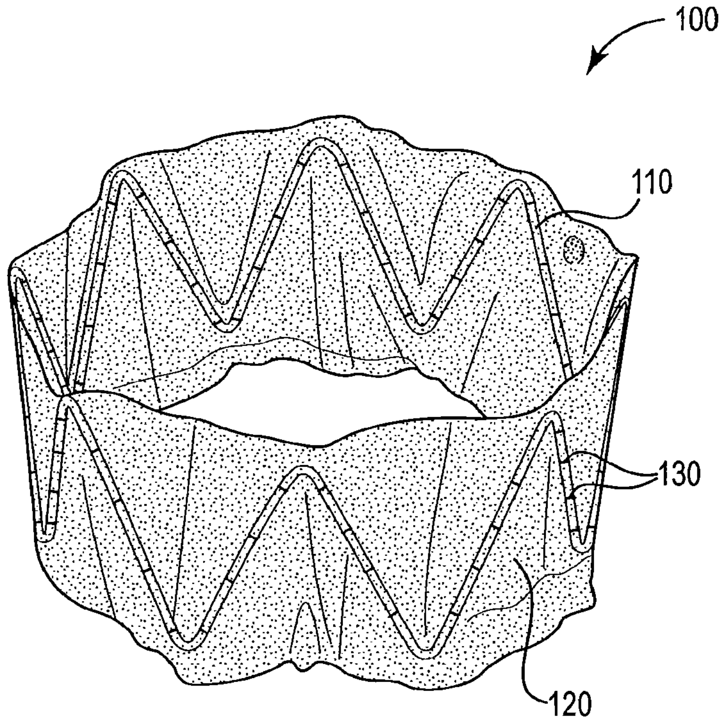
FIG. 1 is a perspective view of a sleeved sinus and nasal stent.

Referring to FIG. 1, stent 100 is shown in perspective view, and includes base stent 110 having a generally tubular configuration formed by bending a length of wire into a zig-zag configuration and connecting the free ends to form a circular hoop. Sleeve 120 surrounds and constrains base stent 110, and may be a smooth- or non-smooth-surfaced, porous or non-porous material. Sleeve 120 may be fastened to base stent 100 using a variety of measures, such as sutures or other stitches 130 distributed at intervals along base stent 110, or may merely held in tension by base stent 100 after installation or both before and after installation. As depicted in FIG. 1, base stent 110 is fully covered by sleeve 120. In another embodiment (not shown in FIG. 1), base stent 110 may be only partially covered by sleeve 120. Stent 100 and the other embodiments disclosed herein may be made in a variety of shapes and sizes, e.g., for human adult, human pediatric or veterinary (e.g., bovine, equine, ovine, porcine, canine or feline) patient use.

Stent 100 is radially expandable. In the embodiment shown in FIG. 1, stent 100 is also radially compressible and radially resilient, in that the stent can repeatedly be converted from its expanded state to its unexpanded state and back by radially compressing and relaxing base stent 110 or by radially compressing and relaxing the generally cylindrical shape defined by sleeve 120. When in an expanded state, stent 100 is sized and shaped for residence in a sinus or nasal cavity or passage without inhibiting the free passage of air, exhalation gases, mucus or other fluids into and out of the sinus or nasal cavity or passage. Stent 100 may be sized and shaped so as to just fit within such cavity or passage when uninstalled and unrestrained, or so as to be slightly compressed when installed in and restrained by such cavity or passage. Prior to installation, stent 100 desirably is radially compressed to a diameter suitable for loading into a hand-held cannula or inserter sized and shaped for delivery and insertion of stent 100 into such cavity or passage. When so compressed, stent 100 typically will have a lower diameter and greater axial length than when it is expanded and unconstrained.

The sinus or naval cavity or passage is "stentable". By this is meant that the cavity or passage has an open (viz., normally air-filled if healthy) space surrounded by hard or soft tissue and whose shape or size can be increased, maintained, prevented or discouraged from decreasing, or at least prevented or discouraged from falling below a threshold level by insertion of the disclosed stent. Such stentable space can be a pre-existing space, a space created, enlarged or altered by a previous surgical procedure, or a space enlarged or altered by a prior stent.

As will be discussed in more detail below, stent 100 and the other embodiments disclosed herein may be drug-eluting or non-drug-eluting. Also the components of the disclosed stents may individually be or may all be biodegradable (e.g., resorbable) or non-biodegradable. For example, base stent 110, sleeve 120 and stitches 130 may all be biodegradable. If both base stent 110 and sleeve 120 are biodegradable, then preferably base stent 110 and sleeve 120 respectively degrade in a manner such that base stent 100 does not cause increased outward pressure upon nearby tissues as sleeve 120 degrades. In another embodiment, base stent 110 may be biodegradable, sleeve 120 may be non-biodegradable and stitches 130 may be biodegradable or non-biodegradable. In yet another embodiment, base stent 110, sleeve 120 and stitches 130 may all be non-biodegradable.

Stent 100 and the other embodiments disclosed herein are "breathable". This refers to elongated stents having sufficient permeability to air or exhalation gases passing along a central axis of the stent (e.g., along the central axis of a hollow tubular base stent) so as to permit use in a sinus cavity without unduly restricting equalization of intracranial pressures, or to permit use in a nasal passage without unduly restricting low intensity breathing, e.g., when patient is seated or otherwise at rest.

The disclosed stents can help reduce the incidence of headaches for patients in which such a stent may be installed. For example, by configuring sleeve 120 so that it surrounds and radially constrains at least a portion of base stent 110, the pressure applied to neighboring tissues by base stent 110 when base stent 110 is in its installed position can be attenuated and the tendency for stent 100 to cause headaches can be reduced or eliminated in susceptible patients compared to a stent made from base stent 110 without sleeve 120.

The disclosed sleeve can provide several additional advantages. During stent insertion, the sleeve can aid the surgeon by imparting added axial rigidity to the stent and reducing drag or other interference between the stent and tissue surfaces proximate the delivery device and the intended implantation site. In its radially expanded delivered or installed state, the disclosed stent and in particular the outer surface of the sleeve can bear against and thereby provide intimate contact with a larger (or if desired in some embodiments a smaller) surface of the adjacent mucosal tissue than would be contacted by the underlying base stent if used without the sleeve. The sleeve can help maintain the stent in position until such time as a resorbable version of the stent degrades naturally or a non-resorbable version of the stent is removed. The sleeve can also provide added mass for drug loading and added surface area and tissue contact area for drug elution in drug-eluting versions of the stent. The installed sleeve, and especially selected non-porous embodiments of the installed sleeve, can also prevent or discourage adhesion development such that upon later removal of the stent, tearing and mucosal re-bleeding may be avoided. The sleeve may also reduce the rate at which degradation of the base stent occurs, thereby reducing aspiration or sneezing out of stent bio-fragments and aiding in the eventual removal of the stent from the treatment site in one intact or more intact piece. During deliberate removal of a non-resorbable stent or premature removal of an absorbable stent, the sleeve may also aid the surgeon in grasping and cleanly removing the stent.

The headache-reducing feature and other features discussed above are different in nature or extent from those of typical sleeved stents (e.g., cardiovascular stents) used in other parts of the body. For example, headache prevention is not a concern for sleeved cardiovascular stents. Sleeved cardiovascular stents usually are designed for long-term (e.g., multi-year) residence in the body, whereas the disclosed sleeved sinus and nasal stents, and especially the degradable embodiments of such stents, typically will have only short-term, temporary residence in the body (e.g., for up to one week, up to two weeks, up to three weeks or up to one month). Sleeved cardiovascular stents typically have a uniform cross-sectional diameter when installed, whereas the disclosed sleeved sinus and nasal stents, and especially the disclosed sinus stents, often will have a nonuniform cross-sectional diameter when installed. A sleeved cardiovascular stent typically contacts nearby tissue over the entire surface of the sleeve, and often relies upon the sleeve to prevent vascular leakage. Due to the non-uniform cross-sectional diameter of, and prevalence of recesses in, sinus and nasal cavities and passages, the disclosed sleeved sinus and nasal stents typically will not contact mucosal tissue over the entire sleeve surface. Also, leakage is not a significant concern for the disclosed sleeved sinus and nasal stents, as among other things they typically will not be exposed to pressurized fluid flow. For the disclosed sleeved sinus and nasal stents, a "leaky" sleeve structure having appreciable porosity or even a plurality of visible openings typically will represent an advantage rather than a disadvantage. A leaky sleeve structure can limit contact with the surrounding tissue and may permit or in some embodiments promote the return of injured, infected, inflamed or surgically repaired tissue to a normal state. Such return to a normal state may occur through one or more healing mechanisms such as modulation of an inflammatory response, phagocytosis, mucosal remodeling, reciliation or other full or partial restoration of normal function. Sleeved cardiovascular stents may rely on the sleeve to prevent long term tissue ingrowth. Some embodiments of the disclosed sleeved sinus and nasal stents can include configurations or coatings to discourage tissue ingrowth. Even where such configurations or coatings are not employed, the typical short residence time in sinus or nasal cavities or passages for the disclosed stents, and especially for biodegradable embodiments of such stents, means that nearby tissues will not have much time to grow into the stent. Desirably the sleeve in the disclosed sinus and nasal stents will permit or at least not discourage natural rhythmic cilia motion (viz., cilia beating) by nearby cilia, and the reciliation of nearby deciliated tissue surface regions. Sleeved cardiovascular stents usually are designed to exert considerable pressure on the surrounding tissue. Exertion of such pressure is of less concern (and may even be a disadvantage) in an ethmoidal stent, and in a frontal or maxillary sinus stent may not be needed at all beyond the pressure required to assure good tissue contact in a drug-eluting stent. In addition, the disclosed sinus and nasal stents typically will contact mucosal tissue (e.g., ciliated mucosal tissue) rather than vascular tissue and thereby will have a different installed environment, different nearby natural defenses and different degradation-inducing conditions than will be the case for a cardiovascular stent.

Figure 2:
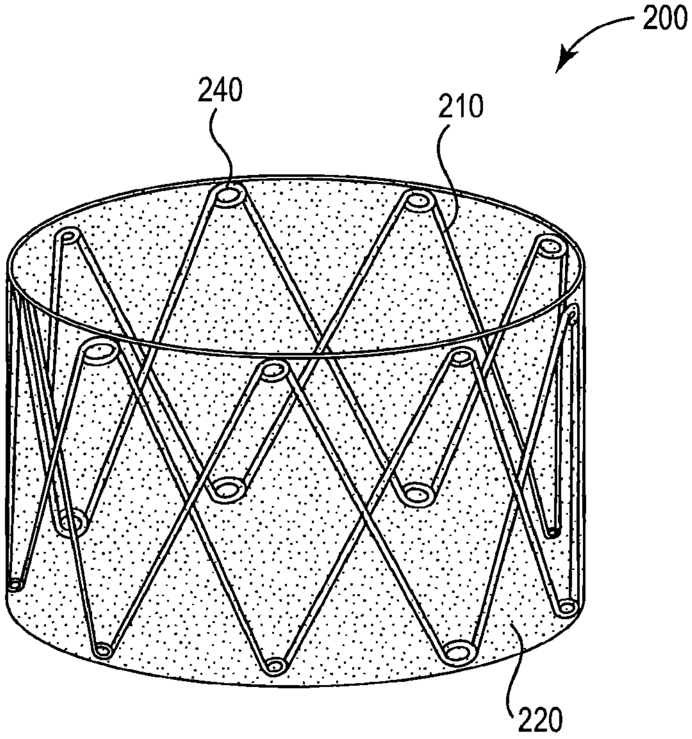
FIG. 2 is a perspective view of another sleeved sinus and nasal stent.
Figure 3:
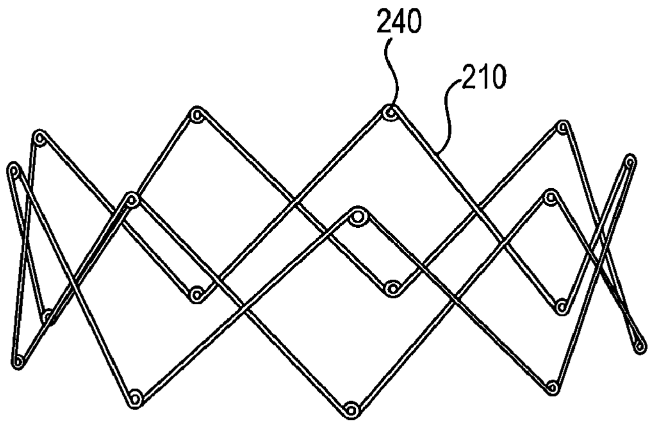
FIG. 3 is a perspective view of the FIG. 2 base stent in an expanded, unconstrained configuration.
Figure 4:
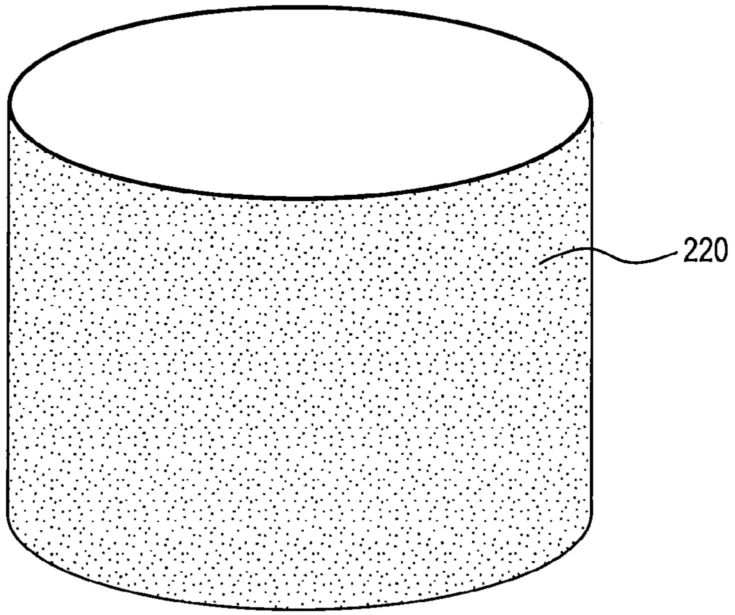
FIG. 4 is a perspective view of the FIG. 2 sleeve.

FIG. 2 through FIG. 4 respectively show perspective views of stent 200, base stent 210 having a generally tubular, zig-zag configuration, and generally tubular constraining sleeve 220. Coil spring loops 240 impart added radial resiliency to base stent 210. Exemplary such base stents are described for example in U.S. Pat. No. 8,585,731 B2 (Abbate et al.). Drug-eluting stents suitable for use as base stent 210 may for example be obtained in two different diameters from Intersect ENT, Inc., as the PROPEL™ stent and the PROPEL Mini stent. Both are biodegradable radially expandable polymeric stents loaded with mometasone furoate, and both are designed to be delivered in compressed form into the ethmoid sinus as is or following functional endoscopic sinus surgery ("FESS"), whereupon they expand, slowly degrade, elute mometasone furoate to nearby tissues, and can help treat conditions such as chronic rhinosinusitis. The original version of the PROPEL stent has a compressed diameter of 5.2 mm for installation and about a 60 mm diameter when unconstrained. The "PROPEL Mini" version is used in patients with less extensive surgery or smaller anatomy, and has a compressed diameter of 4 mm for installation and about a 40 mm diameter when unconstrained. For both PROPEL stents, some patients have reported headaches. In some cases surgeons have addressed this problem by replacing the original version of the stent with the Mini version, and in other cases by prematurely removing the stent and not replacing it. The embodiment shown in FIG. 2 through FIG. 4 provides an alternative solution. By way of example, an original PROPEL stent can be combined with a sleeve 220 having a diameter less than 60 mm, e.g., up to about 55, up to about 50, up to about 45, up to about 40, up to about 30, up to about 20 or up to about 10 mm. Also, a PROPEL Mini stent can be combined with a sleeve 220 having a diameter less than 40 mm, e.g., up to about 35, up to about 30, up to about 25, up to about 20, up to about 10 or up to about 8 mm. As the sleeve diameter is reduced, the likelihood that a headache may result can likewise be reduced. In addition, as the sleeve diameter is reduced, the axial rigidity of the stent during insertion and ease of insertion can likewise be increased. Persons having ordinary skill in the art will recognize that other sleeve dimensions may be used when other base stents or other implantation sites are employed, such as implantation in the maxillary or frontal sinus cavities, or implantation in nasal passages. Persons having ordinary skill in the art will also recognize that other sleeve dimensions may be used for stents designed for installation in pediatric patients or animals.

Figure 5:
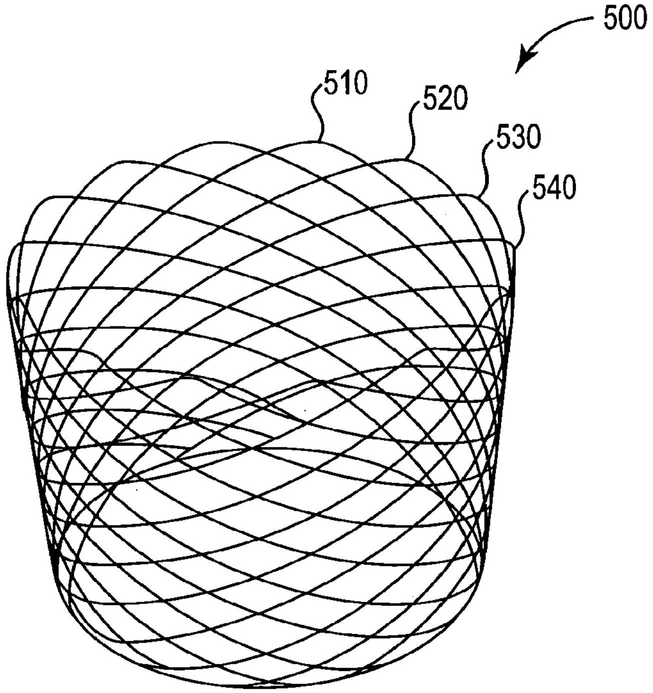
FIG. 5 is a perspective view of another base stent.

FIG. 5 shows a perspective view of base stent 500 having a cage-type configuration formed from a series of intermeshed wires including wires 510, 520, 530, 540 and additional wires not labeled in FIG. 5. Stent 500 may have an elasticity such that it is radially expandable on its own after being radially compressed, or may be relatively inelastic and rely upon the use of a balloon or other internally-inserted expansion device to become radially expanded.

Figure 6:
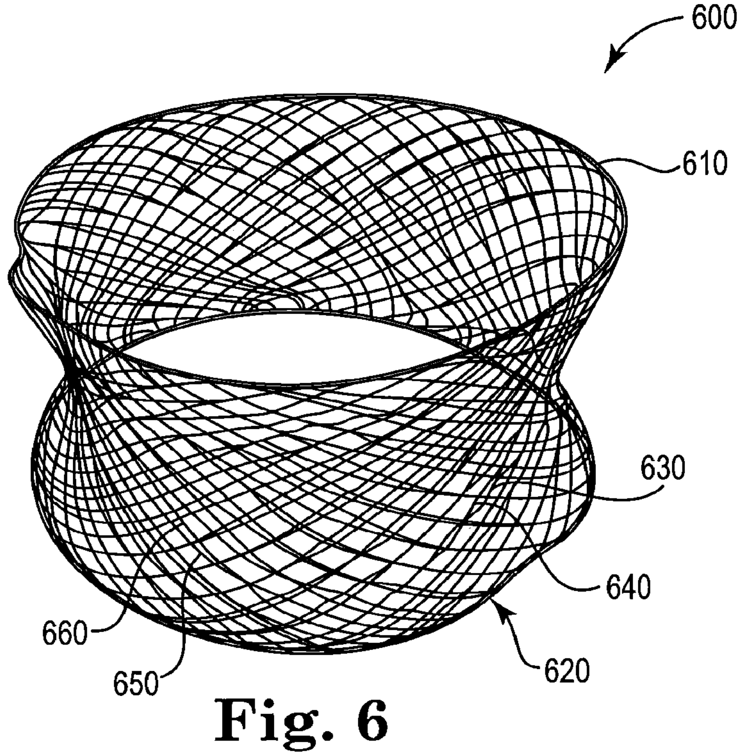
FIG. 6 is a perspective view of a base stent or sleeve.

FIG. 6 shows a perspective view of article 600 which may be either a base stent or a sleeve. Article 600 includes end hoops 610 and 620 that limit expansion of article 600. Paired wires 630, 640 and paired wires 650 and 660 (as well as additional paired wires lot labeled in FIG. 6) are interwoven and pass back and forth between end hoops 610 and 620. Article 600 may be used as a base stent by radially compressing the parallel wires located between end hoops 610 and 620 while ovalizing end hoops 610 and 620 and inclining them with respect to the central longitudinal axis of article 600. Article 600 may also be used as a sleeve by placing it over a base stent such as one of the base stents described herein.

Figure 7:
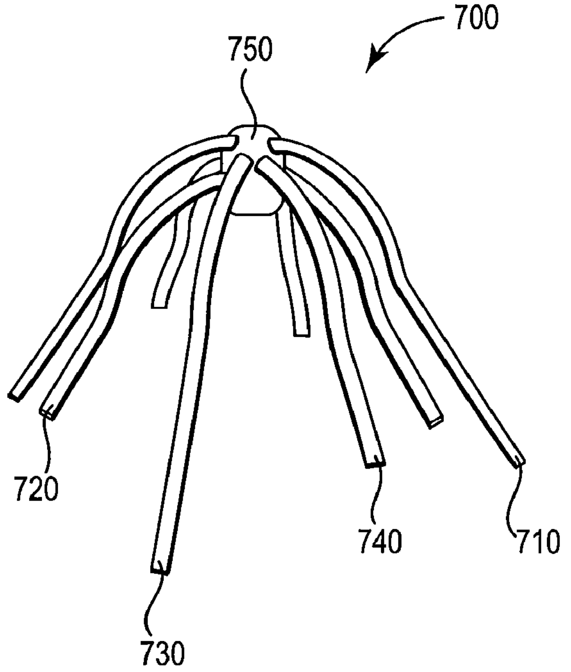
FIG. 7 is a perspective view of another base stent.
Figure 12:
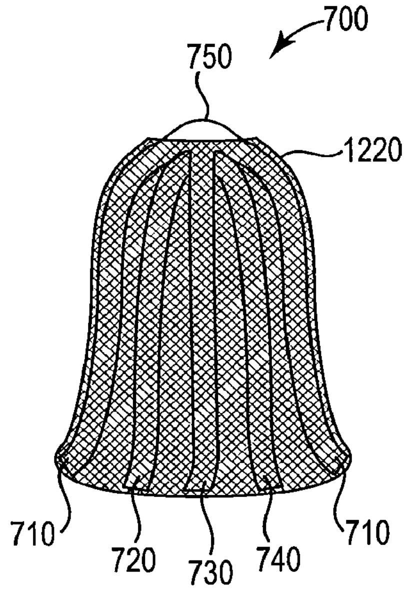
FIG. 12 and FIG. 13 are side sectional views of the FIG. 7 base stent encircled by a full or partial sleeve.
Figure 13:
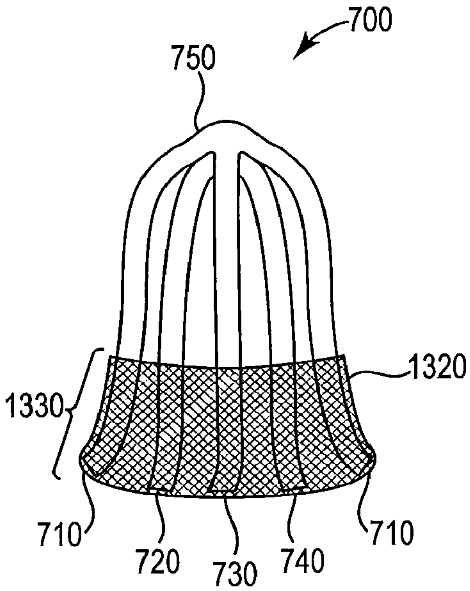

FIG. 7 shows a perspective view of spider-style base stent 700 including legs such as legs 710, 720, 730 and 740 joined to hub 750. Exemplary base stents 700 are described in U.S. Patent Application Publication No. US 2011/0125091 A1 (Abbate). A mometasone furoate-eluting version of such a base stent is currently in clinical trials as the RESOLVE™ stent from Intersect ENT, Inc. According to its manufacturer, the RESOLVE stent has more radial strength than the PROPEL stents in order better to dilate an obstructed sinus, and will release its steroid over a longer period of time. The enhanced radial strength RESOLVE product may also cause unwanted headache symptoms to occur. Such symptoms may be lessened or eliminated by encircling at least a portion of the RESOLVE stent with the disclosed sleeve so as to limit the outward force and outward expansion of the base stent. An exemplary such sleeve is shown in FIG. 12, where sleeve 1220 encircles base stent 700 along the entire length of the legs 710, 720, 730 and 740. Another exemplary sleeve is shown in FIG. 13, where sleeve 1320 encircles only an end portion 1330 of legs such as legs 710, 720, 730 and 740.

Figure 8:
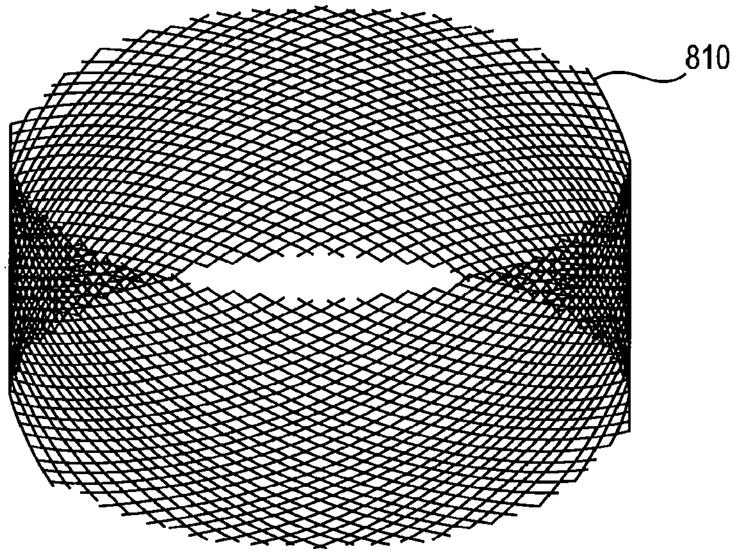
FIG. 8 is a perspective view of another sleeve.

FIG. 8 shows a perspective view of base stent 810 having a woven, open mesh configuration. Base stent 810 may for example be dip-coated in a solution of an elastomeric binder (not shown in FIG. 8) to provide a stent having an elastic sleeve.

Figure 9:
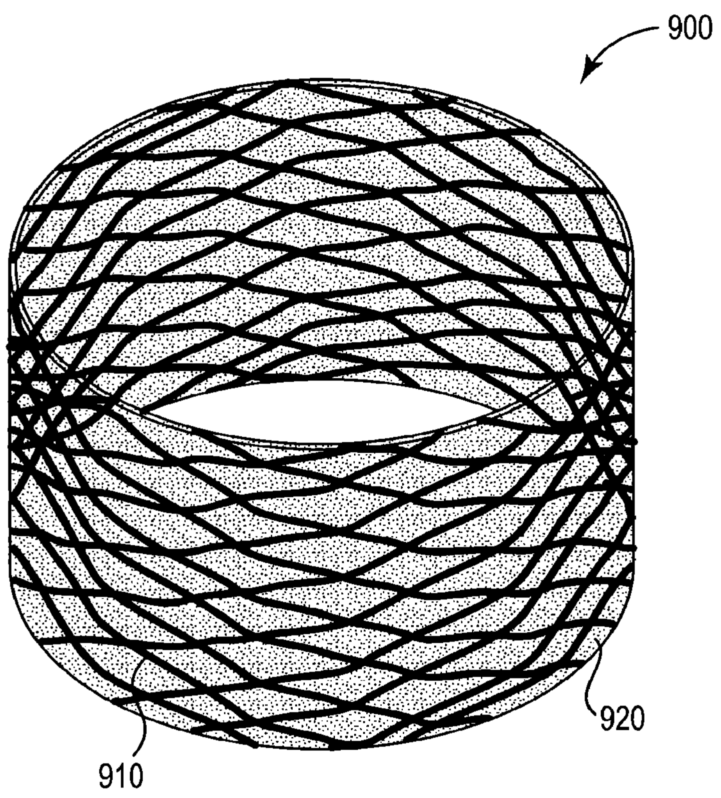
FIG. 9 is a perspective view of another sleeved sinus and nasal stent.

FIG. 9 shows a perspective view of sleeved stent 900 made using such a dip-coating process, by immersing base stent 910 in a solution of an elastomeric binder, and allowing the binder solution to dry and form sleeve 920.

Figure 10:
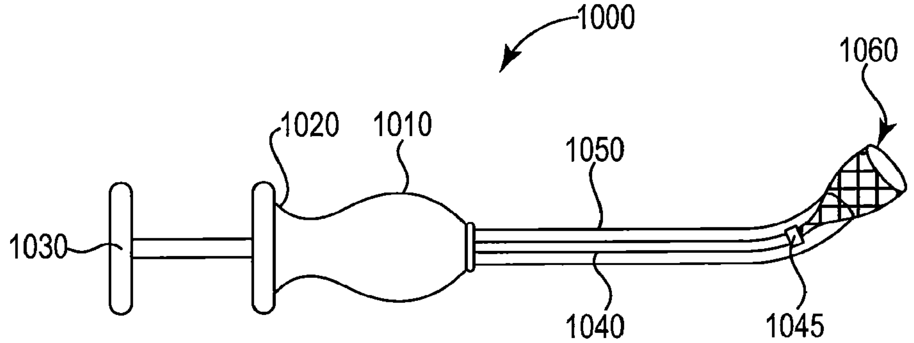
FIG. 10 is a plan view of a loaded insertion device.

FIG. 10 shows a side view, partially in section of an inserter 1000 including grip portion 1010 with finger rest 1020 and thumb press 1030. When thumb press 1030 is advanced toward finger rest 1020, actuator 1040 and its tip 1045 advance through delivery cannula 1050 toward the distal end of inserter 1000 and apply force against the proximal end of stent 1060 pushing stent 1060 out of cannula 1050 and into the intended sinus or nasal cavity or passage. Inserter 1000 and the other inserter embodiments disclosed herein may include colorants, radiopaque or radiographic fillers or other additives in the inserter or in a coating on the inserter to aid in visualization or navigation.

Figure 11:
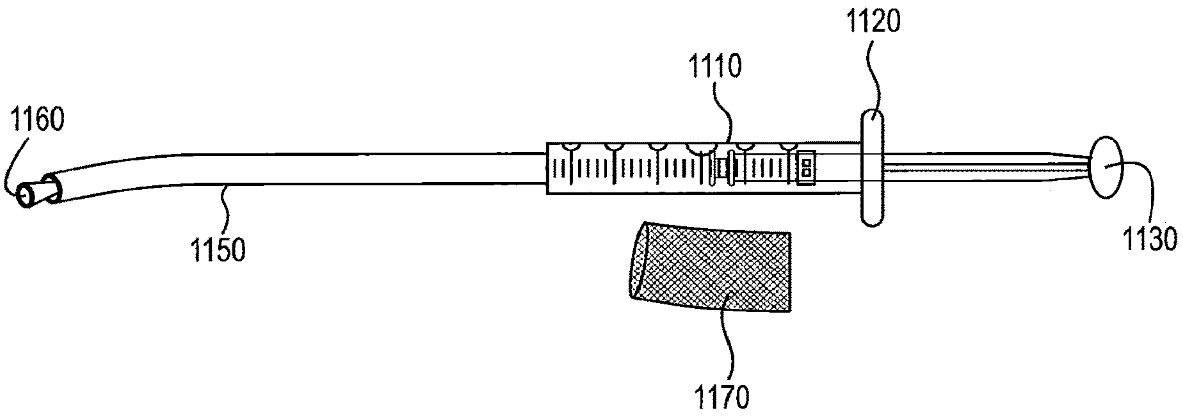
FIG. 11 is a perspective view of an unloaded insertion device and a sleeved sinus and nasal stent.

FIG. 11 shows a side view of an inserter 1100 including barrel portion 1110 with finger rest 1120 and thumb press 1130. Built-in funnel 1160 at the distal end of delivery cannula 1150 may be used to assist in insertion and loading of a radially compressed version of sleeved stent 1170 into delivery cannula 1150. When thumb press 1130 is advanced toward finger rest 1120, an actuator (not shown in FIG. 11) advances through delivery cannula 1150 toward the distal end of inserter 1100 and applies force against the proximal end of the loaded stent so as to push it out of cannula 1150 and into the intended sinus or nasal cavity or passage.

Figure 14:
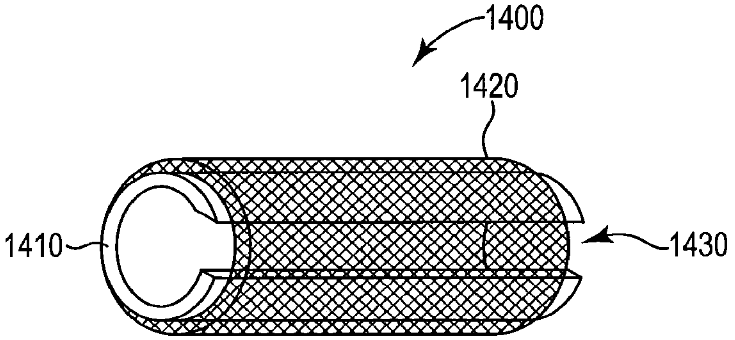
FIG. 14 is a perspective view of an additional sleeved sinus and nasal stent.

FIG. 14 shows a perspective view, partially in section, of a sleeved stent 1400 having a roll-pin style base stent 1410 and sleeve 1420. Base stent 1410 includes a radially compressible and radially resilient generally tubular portion having a C-shaped cross section with a longitudinal opening 1430. Base stent 1410 is surrounded and constrained by sleeve 1420.

Figure 15:
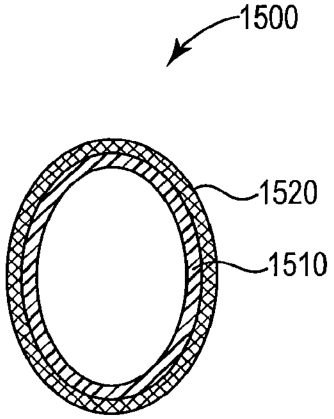
FIG. 15 is an end view of an oval sleeved sinus and nasal stent.
Figure 16:
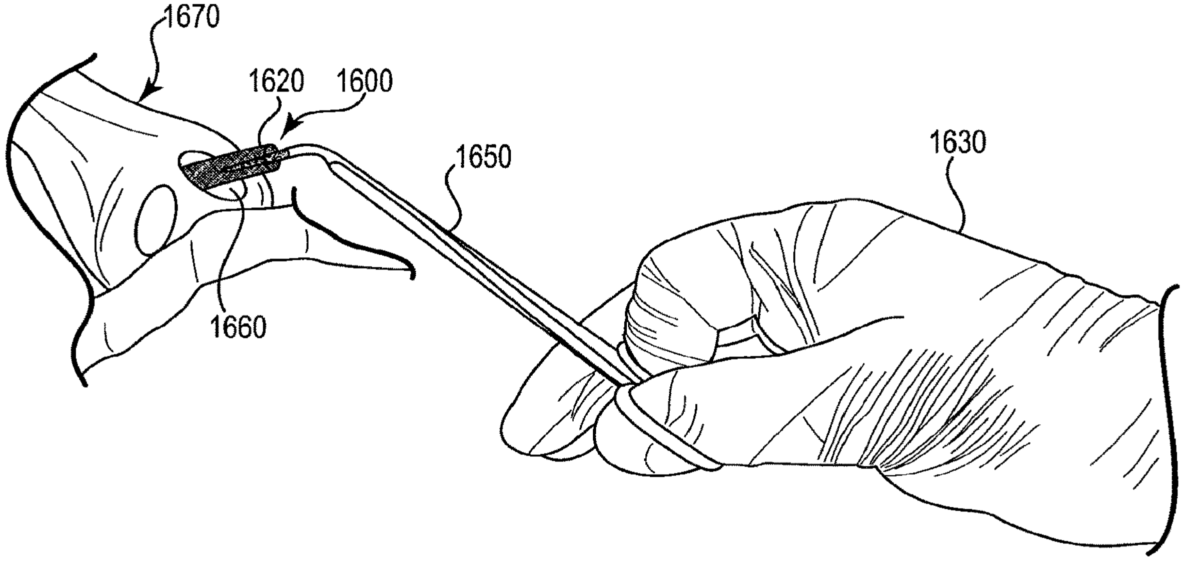
FIG. 16 is a perspective view a sleeved stent gripped in a forceps.

FIG. 15 shows an end view of a sleeved stent 1500 having base stent 1510 and sleeve 1520. Stent 1500 has a generally oval cross-sectional shape rather than the circular cross-sectional shape shown for several of the embodiments described above. Persons having ordinary skill in the art will appreciate that the disclosed stents may be made with yet other cross-sectional shapes FIG. 16 shows a perspective view of stent 1600 whose sleeve 1620 is being gripped and held in a radially-compressed configuration by the gloved hand 1630 of a surgeon holding forceps 1650. Forceps 1650 may be used to deliver stent 1600 into left nostril 1660 of patient 1670 and thence into the nasal passage or if desired into a sinus cavity such as the left ethmoid sinus.

Figure 17:
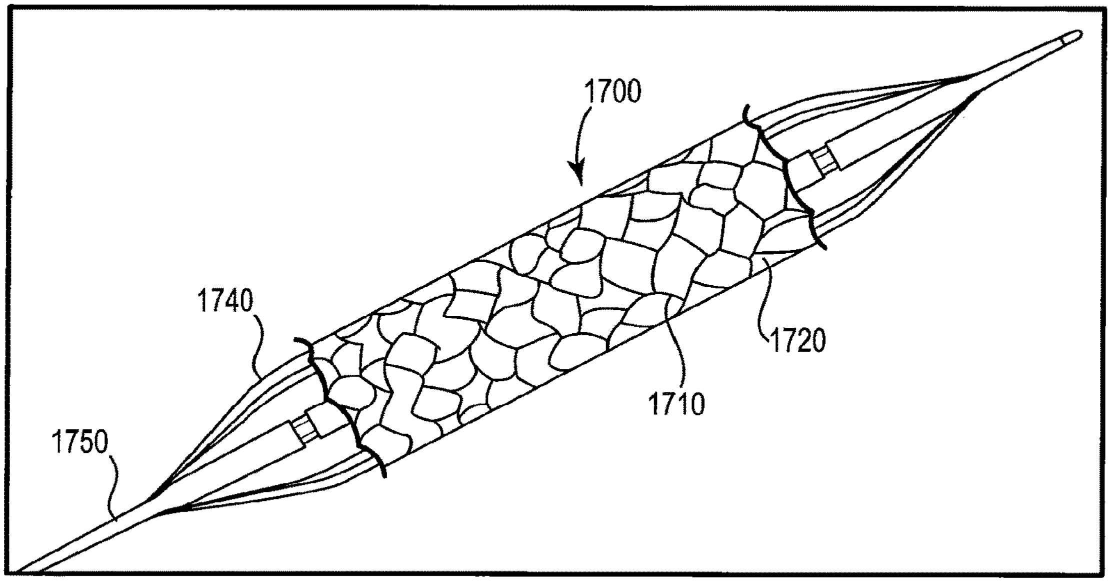
FIG. 17 is a perspective view of a sleeved stent expanded by a balloon.

FIG. 17 shows a perspective view of a radially expanded stent 1700 whose base stent 1710 and sleeve 1720 have been pressed outwardly by inflation of balloon 1740 carried on guide wire 1750.

Figure 18:
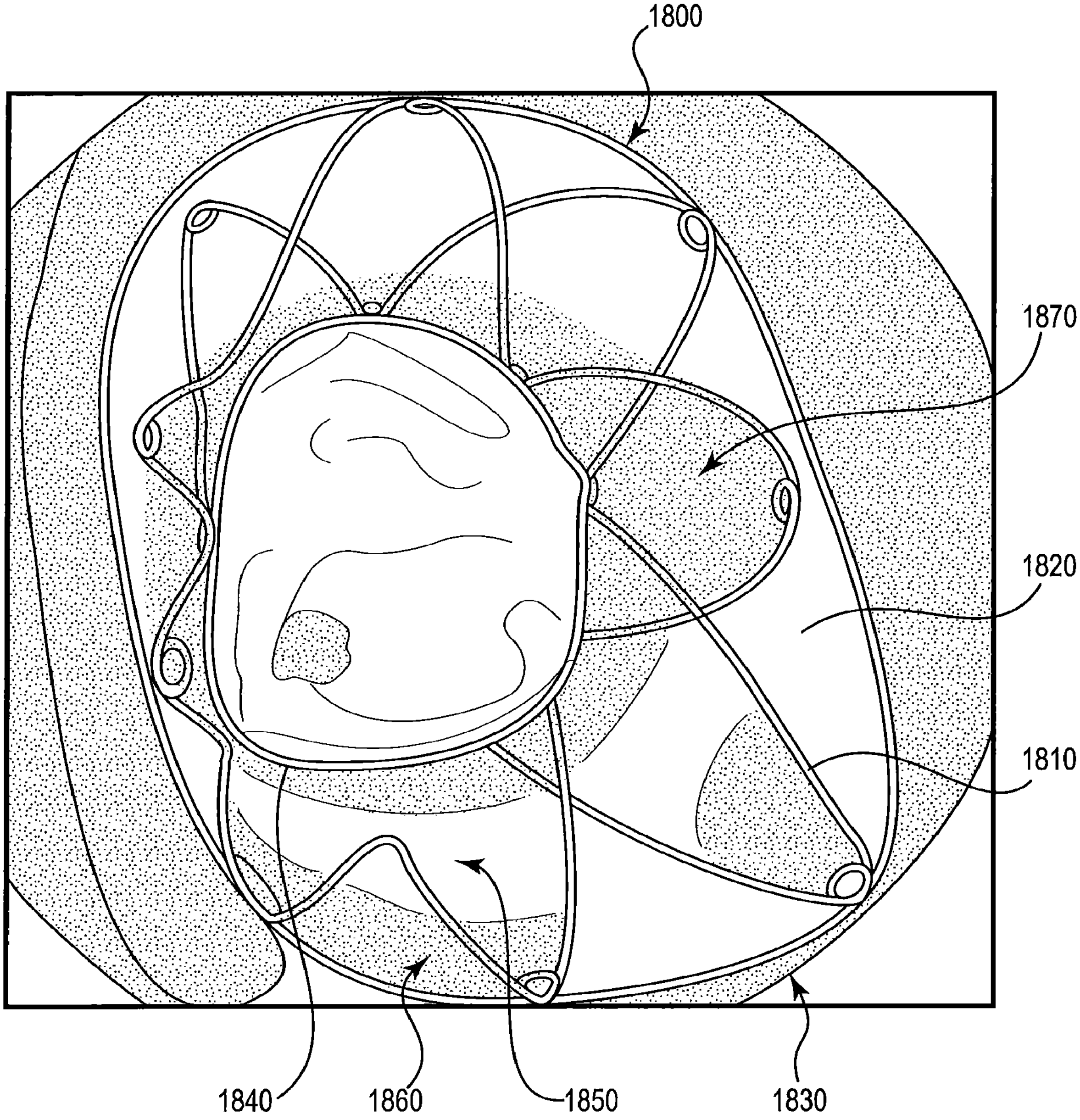
FIG. 18 is a perspective view of a sleeved stent in an ethmoid sinus.

FIG. 18 shows a perspective view, looking from the upper end of a nasal cavity toward the brain, of a sleeved sinus stent 1800 having base stent 1810 and sleeve 1820 installed in an ethmoid sinus 1830. Sleeve 1820 has a generally tapered shape along its lengthwise axis, with a nonuniform cross-sectional diameter that is larger at the proximal end of sleeve 1820 and smaller at the distal end of sleeve 1820. Lighter-colored areas such as regions 1840 and 1850 indicate areas of contact between sleeve 1820 and adjacent mucosal tissue. Darker-colored areas such as regions 1860 and 1870 indicate recesses or other enlarged areas of the ethmoid sinus in which sleeve 1820 does not contact nearby mucosal tissue.

The disclosed base stents may be one or more of flexible, bendable, malleable or resilient when manipulated by hand. In some embodiments the base stent will not be flexible or bendable unless subjected to greater forces than may be applied by hand, such as the forces imparted by a balloon or other expansion device or tool. The base stent may be made using a variety of materials. Exemplary such materials include metallic wires (e.g., stainless steel, titanium, Nitinol and other medically-acceptable metals or alloys) and other natural or synthetic (e.g., polymeric) materials having appropriate caliper, stiffness, malleability and resiliency or non-resiliency. The base stent may be coated with an appropriate drug-eluting polymer to deliver a drug to the intended treatment site. Exemplary non-biodegradable polymers that may be used to fabricate the base stent or provide a drug-eluting coating thereon include acrylonitrile butadiene styrene (ABS), polyacrylates and polymethacrylates (e.g., polymethyl methacrylate or polybutyl methacrylate), nylon, polyolefins (e.g., polyethylene or polypropylene), phosphorylcholine (PC), polystyrene, polycarbonate, non-degradable polyesters, polysulfones, polyethersulfones, polyether block amides (e.g., PEBAX™ from Arkema), thermoplastic elastomers (e.g. C-Flex™ from Saint-Gobain Performance Plastics), fluorinated polymers (e.g. polytetrafluoroethylene) or silicones. Exemplary biodegradable polymers that may be used to fabricate the base stent or provide a drug-eluting coating thereon include synthetic polymers such as polylactic acid (PLLA), poly(lactic-co-glycolic acid) (PLGA), polyglycolic acid, polycaprolactones (PCL) such as poly-ε-caprolactone, degradable polyesters (e.g., polyhydroxypropionate, polyhydroxybutyrate and polyhydroxyvalerate), polyanhydrides, polyorthoesters, degradable polycarbonates, degradable polyamides, polyphosphoesters, polyphosphazenes and polycyanoacrylates, and natural polymers such as polysaccharides, proteins and nucleic acids. Exemplary polysaccharides include agars, alginates, carrageenans, celluloses, chitins, chitosans, chondroitin sulfates, dextrans, galactomannans, glycogens, hyaluronic acids, starches, derivatives (including oxidized polysaccharides and salts) of any of the foregoing, and mixtures of any of the foregoing. The polymer may be uncrosslinked or crosslinked. Additional suitable polymers are described in U.S. Patent Application Publication Nos. US 2007/0014830 A1 (Tijsma et al.) and US 2007/0110788 A1 (Hissong et al.), the disclosures of which are incorporated herein by reference. The base stent may include colorants, radiopaque or radiographic fillers or other additives in the base stent or in a coating on the base stent to aid in visualization or navigation.

Depending on the chosen base stent material, the base stent may be fabricated using a variety of techniques including wire bending, fiber winding, laser cutting, electrical or chemical etching, or injection molding. When a drug-eluting coating is employed, the base stent may be dip-coated, spray coated, or reacted or conjugated with the drug-eluting coating.

The disclosed sleeves may be one or more of flexible, bendable, malleable or resilient when manipulated by hand. In some embodiments the sleeve will not be flexible or bendable unless subjected to greater forces than may be applied by hand, such as the forces imparted by a balloon or other expansion device or tool. The sleeve may be made from a variety of materials including the materials listed above for use in making the base stent. The sleeve may be formed from filamentous strands assembled into a web having a woven, knit or non-woven configuration, or may be formed from a film having a continuous or discontinuous surface. The sleeve may be elastic or inelastic, and if elastic desirably is made from an elastomeric rubbery material such as a silicone rubber or a styrenic block copolymer (e.g., KRATON™ rubber). The sleeve may as mentioned above be formed onto the base stent by dip coating, with synthetic polymers such as PLLA, PLOA, PCL, polyesters, polyanhydrides, polyorthoesters, degradable polycarbonates, degradable polyamides, polyphosphoesters, polyphosphazenes and polycyanoacrylates, and natural polymers such as polysaccharides, proteins and nucleic acids being preferred for making degradable sleeves and the non-degradable polymers mentioned above being preferred for making non-degradable sleeves. The sleeve may include colorants, radiopaque or radiographic fillers or other additives in the sleeve or in a coating on the sleeve to aid in visualization or navigation. The sleeve may be attached to the base stent using a variety of techniques including suturing, heat welding, co-molding, coextrusion, adhesive bonding and solvent bonding. In additional embodiments, the sleeve need not be secured to the base stent using any measures other than the outward pressure exerted on the sleeve by the base stent and any associated frictional forces between them.

In drug-eluting embodiments of the disclosed stent, one or both of the sleeve and base stent may be impregnated, dip coated, spray coated, or conjugated with a medicament or other therapeutic agent. For example, biodegradable or non-biodegradable polymers like those discussed above may be blended with a suitable drug to provide a drug-eluting polymeric coating on the sleeve or base stent. Exemplary therapeutic agents include angiotensin convertin enzyme (ACE) inhibitors; angiotensin receptor blockers (ARBS); antihistamines; corticosteroids (e.g., fluticasones such as fluticasone propionate, mometasones such as mometasone furoate, beclomethasone, triamcinolone, flunisolide, budesonide and ciclesonide); non-steroidal anti-inflammatory agents; chymase inhibitors; cyclooxygenase-2 (COX-2) inhibitors; decongestants (e.g., ephedrine, levomethamphetamine, naphazoline, oxymetazoline, phenylephrine, phenylpropanolamine, propylhexedrine, synephrine, tetrahydrozoline, xylometazoline, pseudoephedrine and tramazoline); matrix metalloproteinase (MMP) inhibitors (e.g., doxycycline, TIMP metallopeptidase inhibitor 1 and dexamethasone); mucolytics; opioids (e.g., methadone, morphine, tramadol and oxycodone); therapeutic polymers and combinations thereof. Additional examples of these and other drug classes and drugs are listed in the above-mentioned Tijsma et al. and Hissong et al. applications. If desired, other therapeutic agents for the treatment or prevention of various conditions may be employed, including analgesics, anti-cholinergics, anti-fungal agents, anti-parasitic agents, antiviral agents, biostatic compositions, chemotherapeutic/antineoplastic agents, cilia enhancement agents (e.g., zinc or magnesium), cytokines, hemostatic agents (e.g., thrombin), immunosuppressors, nucleic acids, peptides, proteins, vasoconstrictors, vitamins, mixtures thereof, and additional other therapeutic agents that will be familiar to persons having ordinary skill in the art. A useful list of such other therapeutic agents may be found, for example, in U.S. Patent Application Publication No. US 2007/0264310 A1 (Hissong et al.), the disclosure of which is incorporated herein by reference. The chosen therapeutic agents will typically be different from agents that sometimes been employed in stents, such as cardiovascular stents, used in other parts of the body. For example, cardiovascular stents may employ anti-proliferative drugs designed to discourage restenosis or smooth muscle growth, such as paclitaxel and rapamycin. The presently disclosed stents need not include anti-proliferative drugs. In some embodiments, sleeves containing any of a variety of drugs or any of a variety of drug loadings are provided separately from the base stent, and an appropriate sleeve is selected and assembled with the base stent on site either during or just prior to surgery, to provide a completed stent having a customized drug loading.

The sleeve or other portions of the disclosed stents may include a coating in the form of a liquid, gel or a soluble or insoluble solid. The coating may for example be a drug-eluting coating to enhance healing, an antimicrobial coating to resist formation of biofilms or other infection markers, a lubricating coating to enhance installation, a hemostatic coating to control bleeding, an adhesive coating to enhance retention, or a cilia growth-promoting coating to enhance reciliation. The coating may for example be on an outer or inner surface of the sleeve, an outer or inner surface of the base stent, or any combination thereof. The coating may be inorganic or organic, and if organic may be uncrosslinked, crosslinkable or crosslinked. For example, a stent having a gel-coated sleeve represents a preferred embodiment.

The disclosed stents are radially expandable, and in some embodiments may also be radially compressible, radially resilient, or both radially compressible and radially resilient. The stents are sized and shaped for residence in a sinus cavity, an opening thereto or a nasal passage, with stents sized and shaped for residence in the ethmoid sinus being preferred and drug-eluting stents sized and shaped for residence in the ethmoid sinus being especially preferred. Compared to locating a drug-eluting stent in a natural ostium, locating a drug-eluting stent in the ethmoid sinus provides a central location that may increase the probability of uniform drug elution within the sinuses, or of drug elution that will reach all desired sites of inflammation. Improved uniformity of drug delivery may be enhanced by the sleeve whose increased contact area with mucosa can permit improved drug uptake into nearby ciliated or other mucosal tissues, e.g., ciliated or other mucosal tissues in contact with the sleeve.

The disclosed stents may have a variety of diameters or average diameters measured perpendicular to the stent's longitudinal central axis. The stent diameter will for example vary dependent upon the intended installation site and patient. A stent for use in an adult human ethmoid or maxillary sinus may for example have an uncompressed diameter (e.g., an average diameter for a stent having a circular or substantially circular cross-section, or a minimum or maximum diameter for a stent having an oval or other non-circular cross-section) less than about 6 cm, than about 5 cm, less than about 4 cm, less than about 3 cm or less than about 2 cm. Such stents may for example have a radially compressed diameter (e.g., an average diameter for a stent having a circular or substantially circular cross-section, or a minimum or maximum diameter for a stent having an oval or other non-circular cross-section) of less than about 1 cm, less than about 9 mm, less than about 8 mm, less than about 7 mm, less than about 6 mm, less than about 5 mm or less than about 4 mm. Expressed using outside diameters from the French catheter scale, these compressed diameters correspond approximately to French Gauge sizes of less than about 30, less than about 26 to 28, less than about 24, less than about 20 to 22, less than about 18, less than about 15 or less than about 12. The same diameters may be used to describe the inside diameter of the hollow tubular portion in the recited inserter. Compressed stent diameters less than about 8 mm (French 24) or less than about 6 mm (French 18) are preferred. Stents for use in an adult human frontal sinus may for example have an uncompressed diameter less about 5 cm, less than about 4 cm, less than about 3 cm or less than about 2 cm, and may for example have a radially compressed diameter of less than about 1 cm, less than about 9 mm, less than about 8 mm, less than about 7 mm, less than about 6 mm, less than about 5 mm or less than about 4 mm. Stents for use in an adult human nasal cavity may for example have an uncompressed diameter less than about 4 cm, less than about 3 cm, less than about 2 cm or less than about 1 cm, and may for example have a radially compressed diameter less than about 1 cm, less than about 9 mm, less than about 8 mm, less than about 7 mm, less than about 6 mm, less than about 5 mm or less than about 4 mm. Persons having ordinary skill in the art will appreciate that for pediatric or animal use, appropriate adjustment of these suggested diameters may be in order.

In some embodiments, the disclosed stents are compressible to a diameter suitable for insertion in and delivery from a handheld delivery cannula or inserter sized and shaped for insertion into the desired sinus or nasal cavity or passage. In other embodiments, the stents are supplied in a compressed form over a balloon other radially expandable device having a guide wire or other suitable inserter sized and shaped for insertion into the desired sinus or nasal cavity or passage.

The disclosed stents may be sized so that they will expand or may be expanded to maintain intimate contact with nearby mucosal tissue, or may be sized so as to be slightly undersized in the intended treatment area and not maintain such intimate contact. In some embodiments the sleeve is sized so that the stent does not contact mucosal tissue over all or even a majority of the sleeve surface. In other embodiments the sleeve is sized so that the stent contacts mucosal tissue over a majority or even all of the sleeve surface. In additional embodiments the sleeve is sized so that the sleeve and stent do not apply outward pressure, or apply less pressure than can be discerned by the patient, against nearby mucosal tissue. The extent to which such pressure may be discerned, may be tolerated or may cause headaches can vary widely from patient to patient, from surgical site to surgical site, from procedure to procedure and from surgeon to surgeon. It accordingly can be desirable to provide the disclosed sleeve in a variety of diameters, for example two, three, four or more diameters, so as to accommodate different patients, surgical sites, procedures or surgeons. It can also be desirable to provide the disclosed sleeve in circular, oval or both circular and oval cross-sectional shapes so as to accommodate different patients, surgical sites, procedures or surgeons. In some embodiments both the sleeve and base stent are provided in a variety of diameters, so as to enable assembly of completed stents in a variety of sizes. In some embodiments the sleeve is taut and essentially wrinkle-free when the stent is installed, and in other embodiments the sleeve may be wrinkled or may have slack regions when the stent is installed. In some embodiments, the disclosed stents have a uniform cross-sectional diameter and shape along their entire length, and in other embodiments the shape or diameter vary along the length of the stent.

In certain preferred embodiments, the base stent, sleeve or both the base stent and sleeve can be manually compressed using a surgeon's thumb and an opposing finger. In certain additionally preferred embodiments, the base stent, sleeve or both the base stent and sleeve will, once such manual compression ends, relax and resume or nearly resume their original dimensions. In certain additionally preferred embodiments, the stent diameter after such relaxation will be appreciably less (e.g., at least 1 mm, at least 5 mm or at least 1 cm less) than the diameter after relaxation of the base stent without the sleeve.

The disclosed stents may have a variety of lengths as measured along the stent longitudinal central axis. The stent length may for example vary dependent upon the intended installation site. By way of example, the original version of the PROPEL stent is said to have a nominal expanded length (which in a typical installation site may correspond to the installed length) of about 23 mm. The PROPEL Mini stent is said to have a nominal expanded length of about 16 mm. A stent for use in the ethmoid sinus may for example have an installed length of about 0.1 cm to about 4 cm, e.g., about 1 cm to about 3 cm or about 1.5 cm to about 2 cm. Stents for use in the frontal or maxillary sinus cavities or the openings thereto may have a variety of lengths, with stents placed in the opening to a frontal or maxillary sinus typically having a shorter length than stents placed in the sinus cavity itself. Frontal or maxillary sinus stents may for example have an installed length of about 0.1 cm to about 5 cm, e.g., about 1 cm to about 4 cm or about 2 cm to about 3 cm. Stents for use in a nasal passage may for example have an installed length of about 0.5 cm to about 6 cm, e.g., about 1 cm to about 5 cm or about 1 cm to about 4 cm. The stent length prior to installation typically will be longer than the installed length and may become shorter when the stent radially expands or is radially expanded during installation. Persons having ordinary skill in the art will appreciate that for pediatric or animal use, appropriate adjustment of these suggested lengths may be in order.

In some embodiments, the entire stent is resorbable and biodegradable, and designed for one-time insertion in a patient. In other embodiments, the sleeve, base stent or both sleeve and base stent are non-resorbable and non-degradable, with the non-degradable portion being designed for insertion in and subsequent removal from a patient.

The stent typically will be packaged with an inserter like those described above. A portion of the inserter will be sized for insertion in a sinus or nasal cavity, and when used for example to treat an adult human, may have a length along the insertable portion of about 1 cm to about 18 cm, about 4 cm to about 12 cm or about 5 cm to about 10 cm. For some stents and surgical sites, an ordinary forceps, for example like that shown in FIG. 16, may be used to install the stent.

Stents having a base stent and sleeve that do not undergo compression set, or that will be radially expanded by a balloon or other expansion device, may be packaged and shipped in a radially compressed state, e.g. inside an inserter or over a balloon. Stents having a base stent or sleeve that may undergo compression set or that are self-expanding desirably are packaged and shipped in an uncompressed state and are placed in an inserter or gripped with a forceps or other compression device at the surgical site. The base stent and sleeve may be assembled together prior to shipment to a surgical site, or may be separately packaged and assembled at such site. In any event, the base stent and sleeve typically will be sealed in suitable packaging (for example, a vial, pouch, bag, box or tray) and subjected to sterilization (using for example heat, gases or radiation) prior to shipment to a surgical site.

The invention is illustrated in the following non-limiting examples, in which all parts and percentages are by weight unless otherwise indicated.

Example 1

Base Stent Construction

A base stent similar to base stent 110 in FIG. 1 was manually fabricated from a length of 0.38 mm diameter 300 series hard stainless steel medical wire (Malin Co., Cleveland, OH). The wire ends were welded together using a UNITEK™ Model 101 welder (3M Unitek, Monrovia, CA). The completed base stent was about 3 cm in diameter with a 32 ° strut angle, 2 cm strut length, 7 peaks and 7 valleys.

Example 2

Polyethylene Sleeve Attachment

A sleeved stent similar to stent 100 in FIG. 1 was formed by wrapping a 2.2 cm×8 cm rectangular piece of 17.8 um thick low density polyethylene film having a layer of LOCTITE™ 3972 light cure adhesive (Henkel Corp., Rocky Hill, CT) spread on the inside surface of the polyethylene film around the Example 1 base stent. The base stent was radially compressed sufficiently to reduce its circumference to about 7 cm so that the polyethylene film ends could be overlapped by about 1 cm. The adhesive was cured using a 10 second UV illumination under a DYMAX™ BLUEWAVE™ 200 UV curing spot lamp (Dymax Corp., Torrington, CT).

Example 3

Coating Formulations

Formulation 1. Poly(ethylene-co-vinyl acetate) (PEVA) beads (Sigma-Aldrich Co., St Louis, MO) containing 40 wt. % vinyl acetate and having a melt index of 8 g/10 min at 190 °C/2.16 kg were used to prepare a 5% (w/v) PEVA solution by dissolving 1 g of PEVA in 20 ml tetrahydrofuran (THF) (Sigma-Aldrich Co.). An 8 mg portion of triamcinolone acetonide (TA) (Sigma-Aldrich Co.) was added and dissolved in the solution.

Formulation 2. PEVA beads and poly(butyl methacrylate) (PBMA) powder having a 337,000 $M_w$ by gel permeation chromatography (Sigma-Aldrich Co.) were used to prepare a solution containing 5% (w/v) PEVA and 2.5% (w/v) PBMA in THF by dissolving 1 g PEVA and 0.5 g PBMA in 20 ml THF. An 8 mg portion of TA was added and dissolved in the solution.

Example 4

Coating Application

In separate runs, 1 mL portions of the Formulation 1 and Formulation 2 coating solutions were spread on the polyethylene sleeves of an Example 2 stent and allowed to air-dry overnight. The coatings were further dried under vacuum at 40 °C for 4 hrs.

Example 5

Radial Force Test

The radial expansion force exerted by the Example 2 stent was measured using an MTS QTest™ 25 compression testing system (MTS Systems, Eden Prairie, MN). The stent was compressed between two parallel stages. The radial expansion force was recorded when the distance between the two stages reached 1 cm, and was found to be 15.2 g.

Example 6

Triamcinolone Acetonide Analysis

TA samples were dissolved in a 40:60 water/methanol solvent system and analyzed using an Agilent Technologies™ 1200 Series high-performance liquid chromatography (HPLC) instrument equipped with an Agilent Eclipse XDB-C18 4.6×150 mm column, using a 10 μl sample injection, 1 ml/min flow rate and UV detection at 250 nm. A standard curve was established using a series of standard solutions at different dilutions.

Example 7

Drug Elution

Figure 19:
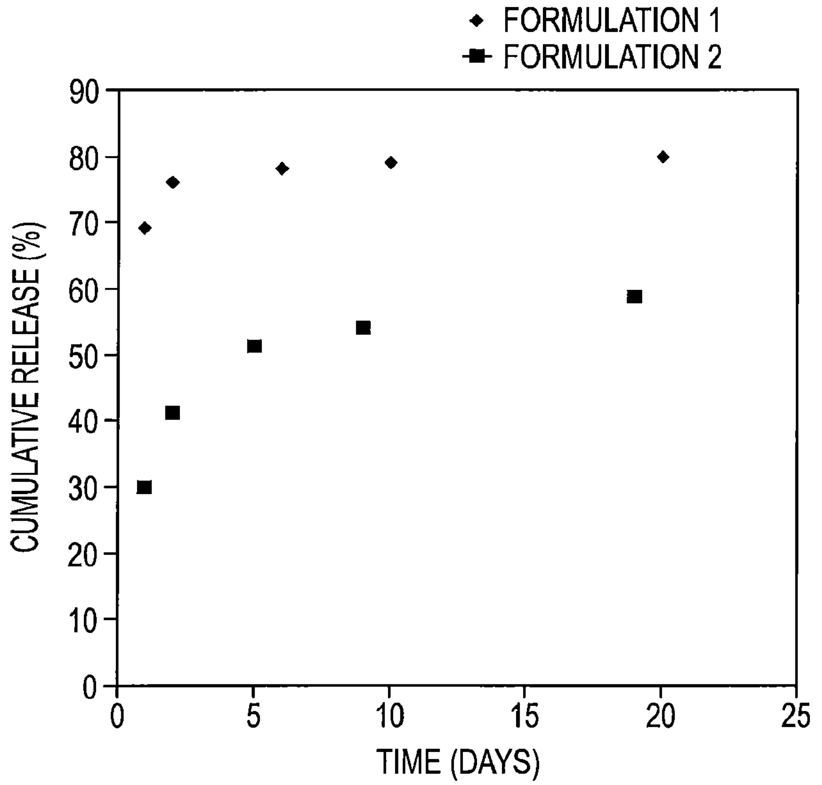
FIG. 19 is a graph showing drug elution as evaluated in Example 7.

A drug elution study was performed in deionized (DI) water at 37 °C by immersing the drug-coated Example 2 stents in 40 mL DI water and incubating the submerged stent at 37 °C. At predetermined times, 1 mL supernatant samples were withdrawn and the TA concentration was measured using HPLC. The cumulative drug release was then calculated. Drug-coated stents were evaluated in triplicate. The results showed that after 1 week, about 80% of the TA eluted from the stent coated with Formulation 1 and about 55% of the TA eluted from the stent coated with Formulation 2. The results are shown in FIG. 19. Formulation 1 provided a more substantial drug “burst” effect compared to Formulation 2. Formulation 2 provided a more constant and potentially longer-lasting drug dose than Formulation 1.

Although specific and in some cases preferred embodiments have been illustrated and described, it will be appreciated by those of ordinary skill in the art that a variety of alternate or equivalent embodiments calculated to achieve the same purposes may be substituted for the specific embodiments shown and described above. This application is intended to cover any such adaptations or variations of the embodiments discussed herein. Therefore, it is manifestly intended that this invention be limited only by the claims and the equivalents thereof.

The invention claimed is:

1. A sleeved stent assembly configured for positioning within a sinus cavity, a nasal cavity, a sinus passage, or a nasal passage, the sleeved stent assembly comprising:

a stent defining a longitudinal axis and first and second end portions spaced-apart along the longitudinal axis, the stent including a hub disposed at the first end portion and a plurality of legs, each leg of the plurality of legs defining a length extending from the hub to a free end of the leg at the second end portion of the stent; and a sleeve disposed about the plurality of legs, the sleeve covering each leg of the plurality of legs over a portion of the length thereof from the free end towards the hub, the portion of the length being less than an entirety of the length.

2. The sleeved stent according to claim 1, wherein each leg of the plurality of legs is biased to extend radially outwardly from the longitudinal axis in a direction along the longitudinal axis from the first end portion of the stent to the second end portion of the stent.

3. The sleeved stent according to claim 1, wherein the sleeve is fastened to the stent.

4. The sleeved stent according to claim 1, wherein the sleeve is held in tension by the stent.

5. The sleeved stent according to claim 1, wherein the plurality of legs is drug-eluting.

6. The sleeved stent assembly according to claim 5, wherein the drug is a corticosteroid.

7. The sleeved stent assembly according to claim 5, wherein the drug includes at least one of a fluticasone, a mometasone, or a triamcinolone.

8. The sleeved stent according to claim 1, wherein the sleeve is drug-eluting.

9. The sleeved stent assembly according to claim 8, wherein the drug is a corticosteroid.

10. The sleeved stent assembly according to claim 9, wherein the drug includes at least one of a fluticasone, a mometasone, or a triamcinolone.

11. The sleeved stent according to claim 1, wherein the sleeve is non-biodegradable.

12. The sleeved stent according to claim 1, wherein the sleeve has a smooth surface.

13. The sleeved stent according to claim 1, wherein the sleeve has a non-porous surface.

14. The sleeved stent according to claim 1, wherein the sleeve is elastic.

15. The sleeved stent according to claim 1, wherein the sleeve is nonwoven.

16. The sleeved stent according to claim 1, wherein the sleeve includes a continuous film.

17. A sleeved stent assembly configured for positioning within a sinus cavity, a nasal cavity, a sinus passage, or a nasal passage, the sleeved stent assembly comprising:

a stent defining a longitudinal axis and first and second end portions spaced-apart along the longitudinal axis, the stent including a hub disposed at the first end portion and a plurality of legs, each leg of the plurality of legs extending from the hub to a free end of the leg at the second end portion of the stent, wherein each leg of the plurality of legs is biased radially outwardly to an expanded position; and a sleeve disposed about at least a portion of each leg of the plurality of legs, the sleeve inhibiting expansion of each leg of the plurality of legs to the expanded position such that each leg of the plurality of legs is maintained by the sleeve in a less-expanded position that is radially inwardly spaced from the expanded position.

18. The sleeved stent according to claim 17, wherein at least one of the sleeve or the plurality of legs is drug-eluting.

19. The sleeved stent according to claim 17, wherein the sleeve is fastened to the stent.

20. The sleeved stent according to claim 17, wherein the sleeve is held in tension by the stent.

* * * * *